United States Patent [19]

Ott

[11] Patent Number: Plant 6,416

[45] Date of Patent: Nov. 22, 1988

[54] GERANIUM PLANT NAMED SCARLET RED VERONICA

[76] Inventor: Cleveland Ott, 677 Grater Ave., Graterford, Pa. 19426

[21] Appl. No.: 938,464

[22] Filed: Dec. 5, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Paul & Paul

[57] ABSTRACT

A new variety of geranium plant is distinguished from its parent, Veronica, (U.S. Plant Pat. No. 5,054) by the color of the petals. The upper side of the petals of the parent Veronica, is Red-Purple Group 58B (R.H.S.). The major outer portion of the upper side of the petals in the new variety is Red Group 46B (R.H.S.) the medial portion is Red Group 44C (RHS), a blotch of Red Group 53C is between the areas of Red Group 46B and 44C, the base portion where the petal joins the stem has a blotch of white, forming with the other petals of the corolla a white eye, and the underside of the petals is Red Group 41A.

2 Drawing Sheets

BACKGROUND OF THE NEW PLANT

The new variety of geranium plant was discovered by applicant as a sport in a bed of zonal geraniums known by the varietal name of Veronica, (U.S. Plant Pat. No. 5,054). The discovery was made in May 1985 in applicant's greenhouse near Graterford, Pa.

The new variety was first asexually reproduced by cuttings at applicant's greenhouse in Graterford, Pa., and has been repeatedly asexually reproduced at that location. It has retained its distinctive characteristics through successive reproduction.

The new variety, when grown in a greenhouse in Graterford, Pa., using natural light and 62° F. night temperatures and 70° F. day temperatures has a response time of six weeks from a well-rooted cutting to a flowering plant in a 4-inch (10 cm) pot.

DESCRIPTION OF THE DRAWING

The drawing comprises two different photographic reproductions in color of the new variety of geranium plant. One photograph is a perspective view of the potted new geranium plant. The other photograph is an enlarged close-up view of the flower. The color in the photographs is as nearly true as is possible with color illustrations of this type.

DESCRIPTION OF THE NEW PLANT

Except for the color of the petals, the new variety of geranium plant has the same characteristics as its parent known by the varietal name Veronica (U.S. Plant Pat. No. 5,054).

In the parent, the upper side of the petals has a color in the Red-Purple Group 58B on the RHS Colour Chart of The Royal Horticultural Society of London. At the base of the petals, the color is Orange-Red Group 33C. All petals include a blotch of Red-Purple 66B.

In the new variety, on the upper side of the petals, the innermost portion has a sizeable blotch of white, forming with the other petals of the corolla a white eye. The medial portion of the petals is Red Group 44C (RHS) while the major outer portion is Red Group 46B (RHS). At least the top three petals include a blotch of Red Group 53C (RHS) between the areas of Red Group 44C and 46B. The underside of the petals in the new variety is Red Group 41A (RHS) which on the HCC chart is Vermilion HCC18.

Other than color, the characteristics of the new variety, which has been given the name "Scarlet Red Veronica", are essentially the same as in the parent (U.S. Plant Pat. No. 5,054). For the convenience of the reader, the characteristics which are common to both the parent and the new variety are set forth below.

It is to be particularly noted that the new variety has non-shattering flower persistence. This is also true of the parent, Veronica. However, prior to my discovery, there has not been a good scarlet red geranium plant with non-shattering flower persistence.

The Plant

Classification:

*Botanical.*—*Pelargonium hortorum,* Bailey.

*Commercial.*—Zonal geranium.

Form: Bush.

Height: 14 to 20 cms. (17 cms. avg.) as a 4-inch pot plant excluding bloom and 24 to 30 cms. (27 cms. avg.) as a 4-inch pot plant including bloom.

Growth: Short and compact plant with more basal branching, closer internodes and smaller leaves as compared with common zonal geraniums.

Strength: Very sturdy and not susceptible to wind and rain damage.

Foliage: The quantity of foliage is of below average abundance.

Leaves:

*Size.*—10 to 12 cms. across.

*Shape.*—Reniform with oblique base.

*Margin.*—Crenate.

*Texture.*—Leathery and pubescent.

*Color.*—Upper side Green Group 137A; under side Green Group 138B.

*Ribs and veins.*—Palmate.

Petioles: 10 to 12 cms.

Stem:

*Color.*—Yellow Green Group 144B.

*Internodes.*—Very short, on the order of 1 cm.

The Bud

Shape: Umbel formed with approximately 50 florets.

Size: As bud develops to color described, head size is 3 cms. in diameter and it opens into a head size of 10 cms. in diameter.

Inflorescense

Blooming habit: Continuous throughout the year.
Size: About 10 cms.
Borne: Singly in an umbel form.
Florets:
*Form.*—Flat with very little cup-shaped and symmetrical in shape with smooth edges.
*Petals.*—7 to 8 in number plus 6 to 7 petaloids.
*Size.*—3 to 4 cms. across.
*Texture and appearance.*—Firm and satiny.
Petaloids:
*Quantity.*—6 to 7 in number.
*Shape.*—Small and twisted.
Pedicel:
*Length.*—1 to 2 cms.
Peduncle:
*Length.*—12 to 20 cms.
Persistence: Nonshattering flower.
Disease resistance: Average to slightly better to Botrytis.
Lasting quality: On the order of three weeks.

Reproductive Organs

Stamens:
*Anthers.*—Approximately 8 arranged cylindrically and carried at a height shorter than the stigma.
*Filaments.*—Pure white to red at the tips; 0.6 cms. in length; flattened.

*Pollen.*—Yellow in color.
Pistils:
*Number.*—1.
*Length.*—1 cm.
*Stigma.*—5 arms reflex back; reddish in color.
*Style.*—White.
Ovaries: Green; 5 carpels.
Fruit: Nonfertile.

The new variety, like its parent, is a short and compact plant. There are more basal branching and close internodes and small leaves as compared with the standard bush zonal geraniums produced in the United States. A short flower stem positions the flower immediately atop of the foliage into the plants and renders the plant very resistant to wind and rain damage. The scarlet red coloring of the petals of the new variety is accentuated by the blotch of white at the base of the petals where the petals join the stem, forming with the other petals of the corolla a white eye.

I claim:

1. A new and distinct variety of geranium plant characterized in that, as distinguished from its parent plant, Veronica, (U.S. Plant Pat. No. 5,054), the major outer portion of the upper side of the petal is Red Group 46B on the RHS Chart, the medial portion is Red Group 44C, a blotch of Red Group 53C is between the areas of Red Group 46B and 44C, the base portion where the petal joins the stem has a white blotch, forming with the other petals of the corolla a white eye, and the under side of the petal is Red Group 41A (RHS), Vermilion HCC18 on the HCC chart.

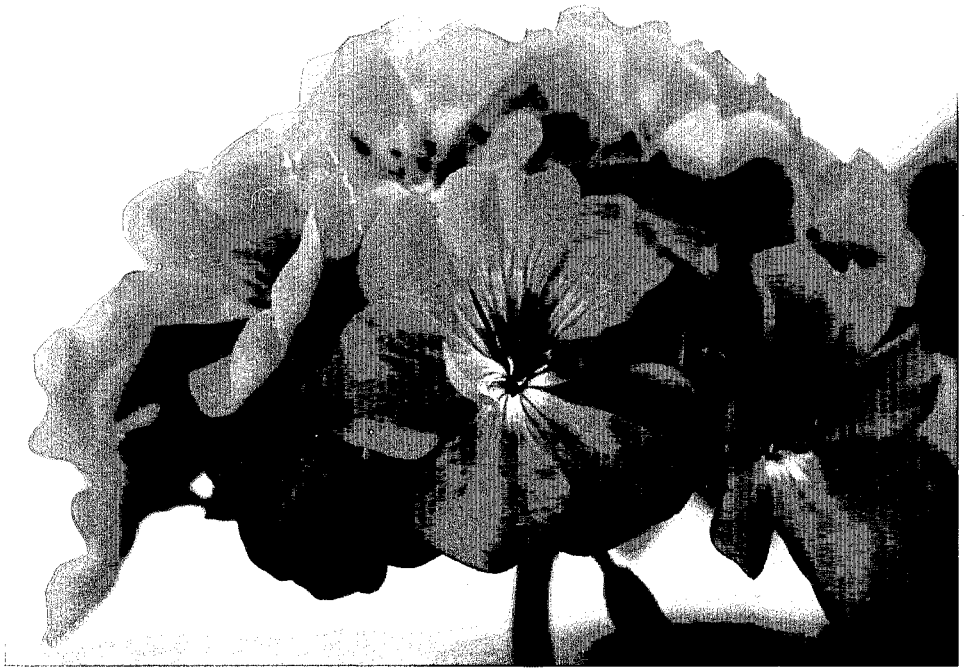

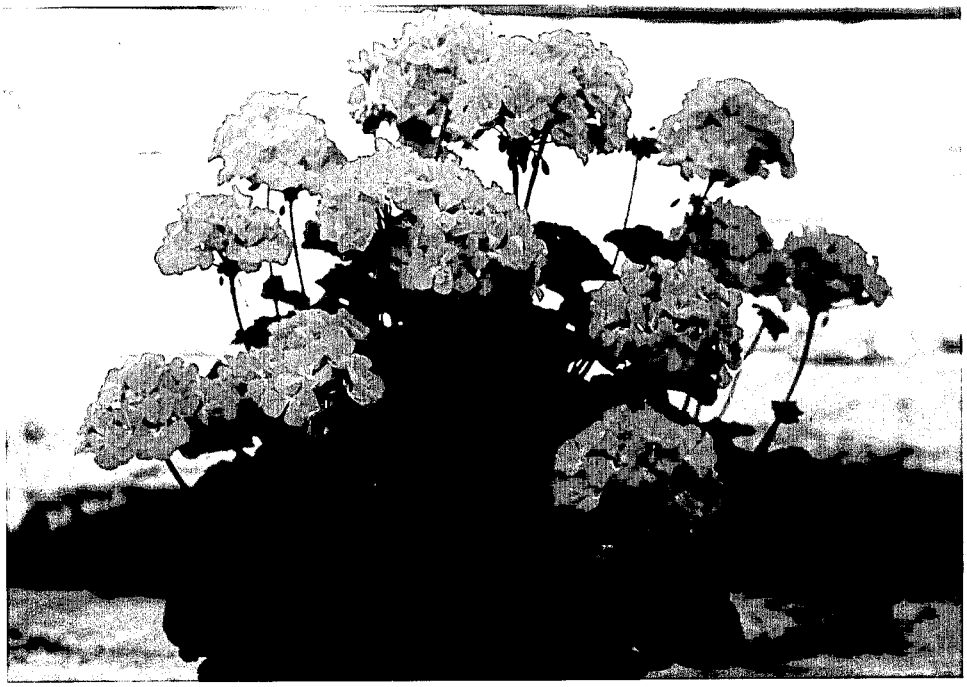

* * * * *